United States Patent
Schaldach et al.

(10) Patent No.: US 6,726,713 B2
(45) Date of Patent: Apr. 27, 2004

(54) METHOD AND DEVICE FOR CRIMPING A STENT

(75) Inventors: Max Schaldach, deceased, late of Erlangen (DE); by Max Schaldach, Jr., legal representative, Berlin (DE); Detlef Behrend, Rostock (DE); Klaus-Peter Schmitz, Rostock (DE); Heinz Mueller, Erlangen (DE); Daniel Lootz, Warnemuende (DE); Dietmar Esperschidt, Fuerth (DE)

(73) Assignee: Biotronik Mess- und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 262 days.

(21) Appl. No.: 09/923,808

(22) Filed: Aug. 7, 2001

(65) Prior Publication Data

US 2002/0035390 A1 Mar. 21, 2002

(30) Foreign Application Priority Data

Aug. 9, 2000 (DE) .......................... 100 39 617
Sep. 19, 2000 (DE) .......................... 100 46 528

(51) Int. Cl.⁷ .................................. A61F 2/06
(52) U.S. Cl. ...................... 623/1.11; 606/191
(58) Field of Search ................ 623/1.11, 1.12; 606/191, 198

(56) References Cited

U.S. PATENT DOCUMENTS

| | | | |
|---|---|---|---|
| 5,709,713 A | * 1/1998 | Evans et al. ................ 623/1.53 |
| 5,836,952 A | 11/1998 | Davis et al. | |
| 5,855,565 A | * 1/1999 | Bar-Cohen et al. ......... 604/104 |
| 6,063,102 A | * 5/2000 | Morales ....................... 606/198 |
| 6,074,381 A | 6/2000 | Dinh et al. | |
| 6,082,990 A | * 7/2000 | Jackson et al. ............. 425/517 |
| 6,092,273 A | 7/2000 | Villareal | |
| 6,125,523 A | * 10/2000 | Brown et al. ................. 29/516 |
| 6,296,661 B1 | * 10/2001 | Davila et al. ............. 623/1.13 |
| 6,346,118 B1 | * 2/2002 | Baker et al. ............... 623/1.12 |
| 6,360,577 B2 | * 3/2002 | Austin ......................... 72/402 |
| 6,481,262 B2 | * 11/2002 | Ching et al. ................... 72/416 |
| 2002/0161426 A1 | * 10/2002 | Iancea ....................... 623/1.11 |
| 2003/0056360 A1 | * 3/2003 | Brown et al. ................. 29/516 |

FOREIGN PATENT DOCUMENTS

EP  0 938 880 A2  9/1999
WO  WO00/21464 A1  4/2000

* cited by examiner

Primary Examiner—Kevin T. Truong
Assistant Examiner—Bradford C Pantuck
(74) Attorney, Agent, or Firm—Hahn Loeser + Parks LLP; Stephen L. Grant

(57) ABSTRACT

The invention concerns a method and a device for crimping a stent onto a balloon of a balloon catheter. The stent is arranged on the balloon so that an outside surface of the balloon and an inside surface of the stent contact each other to form a combination of balloon and stent. The combination is compressed to crimp the stent onto the balloon. The invention is distinguished in that the combination is compressed to varying degrees along the longitudinal axis of the combination.

9 Claims, 6 Drawing Sheets

METHOD AND DEVICE FOR CRIMPING A STENT

The invention concerns a method and a device for crimping a stent onto a balloon of a balloon catheter, wherein the stent is arranged on the balloon in such a way that the outside surface of the balloon and the inside surface of the stent are in contact with each other in order to form a combination of balloon and stent, the combination being compressed to crimp the stent onto the balloon.

BACKGROUND OF THE ART

Methods and devices of this kind are known in the prior art. They serve to produce a combination comprising the balloon of a balloon catheter and a stent which is crimped on the balloon. That makes it possible to move the stent of reduced outside diameter at its desired position on the balloon by means of the catheter into the region of the stenosis to be dilated, and at the same time to hold the stent on the balloon in fixed relationship.

In the methods and devices known in the prior art, the stent, for crimping on the balloon, is compressed by radially inwardly acting forces until it is carried fixedly on the balloon, but can still be deployed by inflation of the balloon in order to be fitted into the internal vessel wall of a stenosis in order to support it. Such a method and a device are known, for example, from U.S. Pat. No. 5,836,952, to Davis (Nov. 18, 1998).

One disadvantage with the prior methods and devices is that the edges of the stents can stick out, or can be bent out, when the stent has to be passed in part through tight narrow vessel curvatures when the combination is inserted through the vessels of the body to the stenosis. When this occurs with regard to segmented stents, it is referred to as the "fish scaling" effect, and it results in damage to the internal walls of the corresponding vessels or in the stent coming into hooking engagement with the vessel wall and possibly being displaced on or being caused to slip off the catheter balloon, which can result in deposits or ruptures of the vessels.

Therefore an object of the present invention is to provide a combination of stent and balloon or a method and a device for crimping a stent on a balloon, which avoid the above-mentioned disadvantages and which securely bring the stent to its implantation location.

SUMMARY OF THE INVENTION

In accordance with the invention that object is attained by a method, a crimping device and a combinations as set forth in the accompanying claims.

The advantages of the present invention are in particular that the fish scaling effect can be avoided or reduced by the fact that the two axial ends of the stent are bent inwardly. As a result, in particular the edges of segments of the stent, which are arranged in succession in the axial direction of the stent, bear against the balloon, even in the procedure for inserting a catheter carrying the combination through narrow winding vessels. The risk of damage to the internal vessel wall is thus reduced, like also the thrust force required for inserting such a balloon catheter or such a combination. In addition, it is also advantageous that the invention provides that the adhesion between the stent and the balloon is increased so as to prevent the stent from inadvertently sliding off the balloon upon insertion of the combination into the vessel in the body.

Advantageous embodiments of the method and the device according to the invention use rollers or plates which are at an alternately increasing and decreasing spacing relative to each so that a combination of stent and balloon which is clamped and compressed between the rollers or plates is crimped to differing degrees along the longitudinal axis of the combination.

The invention can be carried into effect in a particularly advantageous manner by the rollers or plates being provided with a corrugated surface. If now a combination of stent and balloon is forced through between rollers of that kind, the stent is crimped onto the balloon more strongly by the crests of the corrugation than by the troughs of the corrugation. The same applies in regard to compression by means of two plates arranged in parallel relationship. In that case the mutually facing surfaces of the plates are also corrugated in a wave-like configuration in a regular sequence. For the purposes of crimping the stents the two plates are moved towards each other at the same time displaced uniformly relative to each, whereby the combination of stent and balloon is compressed and thus the stent is crimped onto the balloon.

As an alternative it is also possible to use special profiled rollers in 2-, 3- or multi-point rolling devices, straight as well as inclined, to produce the crimping effect. As a further alternative for the invention it is possible to use collet chuck devices with a specially shaped internal clamping liner or also dies which are shaped according to the desired crimping profile. Finally it is also possible to provide for irregular crimping in accordance with the invention with the stent being locally enclosed with aperture-like shutter members.

A further advantageous embodiment of the crimping device according to the invention is distinguished in that for the crimping operation the stent-catheter combination is positioned in an entry nip or pinch between a first roller and a second roller which is arranged in adjacent parallel relationship with the first roller, and there is compressed in the entry nip by means of a third roller arranged in substantially parallel relationship with the other two rollers, at least one of the roller being provided with a corrugated surface. For that purpose, the third roller is preferably driven in rotation about its longitudinal axis. In a preferred embodiment the first and second rollers are supported rigidly while the third roller is mounted pivotably about the first roller by means of a lever connecting the first and third rollers so that in that way the stent-catheter combination positioned in the entry nip between the first and second rollers is compressed and thus crimped in the entry nip by pivotal movement of the lever and the third roller.

Further advantageous embodiments of the invention are set forth in the appendant claims.

BRIEF DESCRIPTION OF THE DRAWINGS

The invention will be better understood when reference is made to the accompanying drawings, where identical parts are identified by identical reference numbers, and wherein.

DETAILED DESCRIPTION OF THE INVENTION

Figure 1:
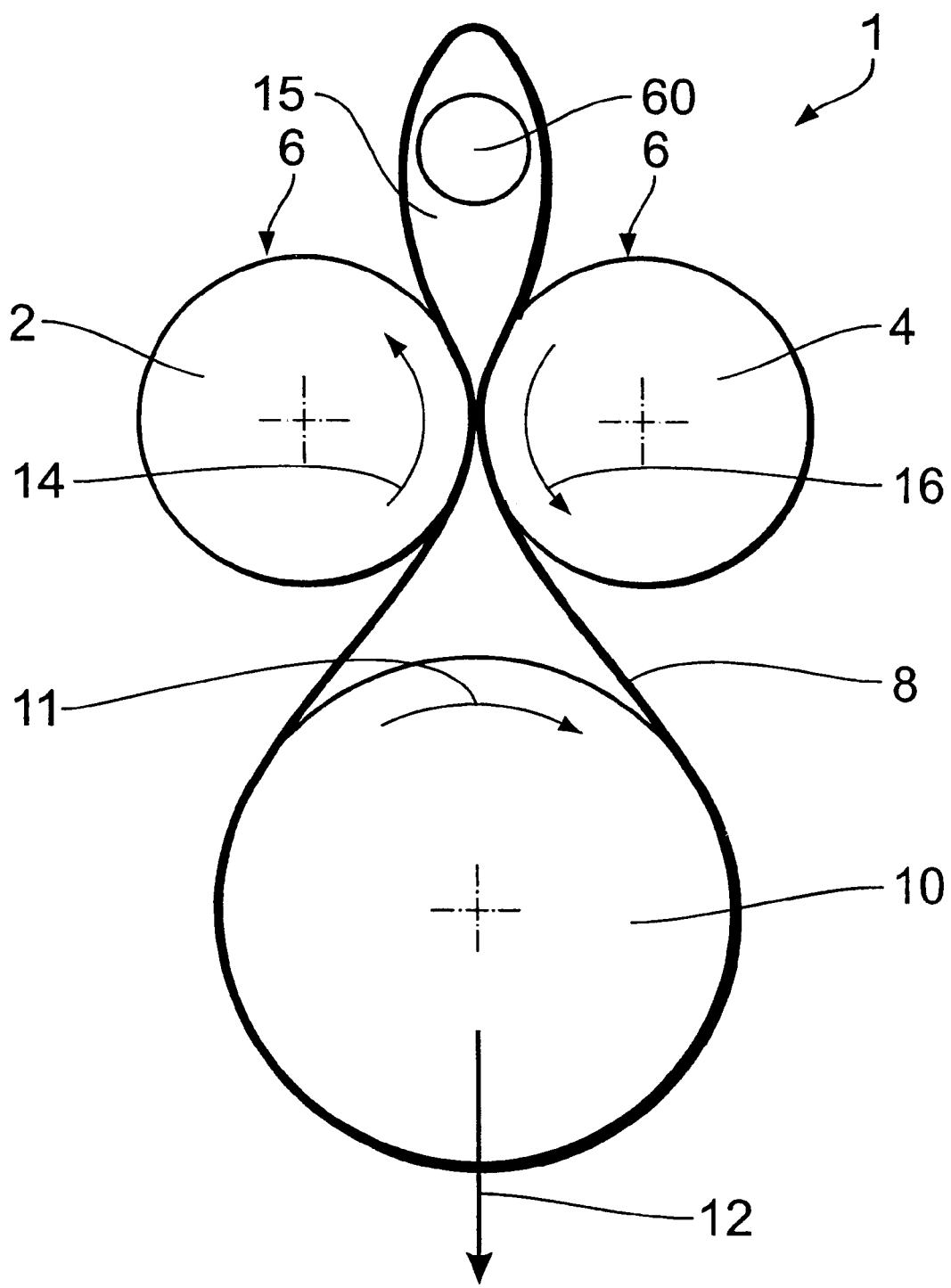
FIG. 1 shows a first embodiment of a crimping device according to the invention.
Figure 1A:
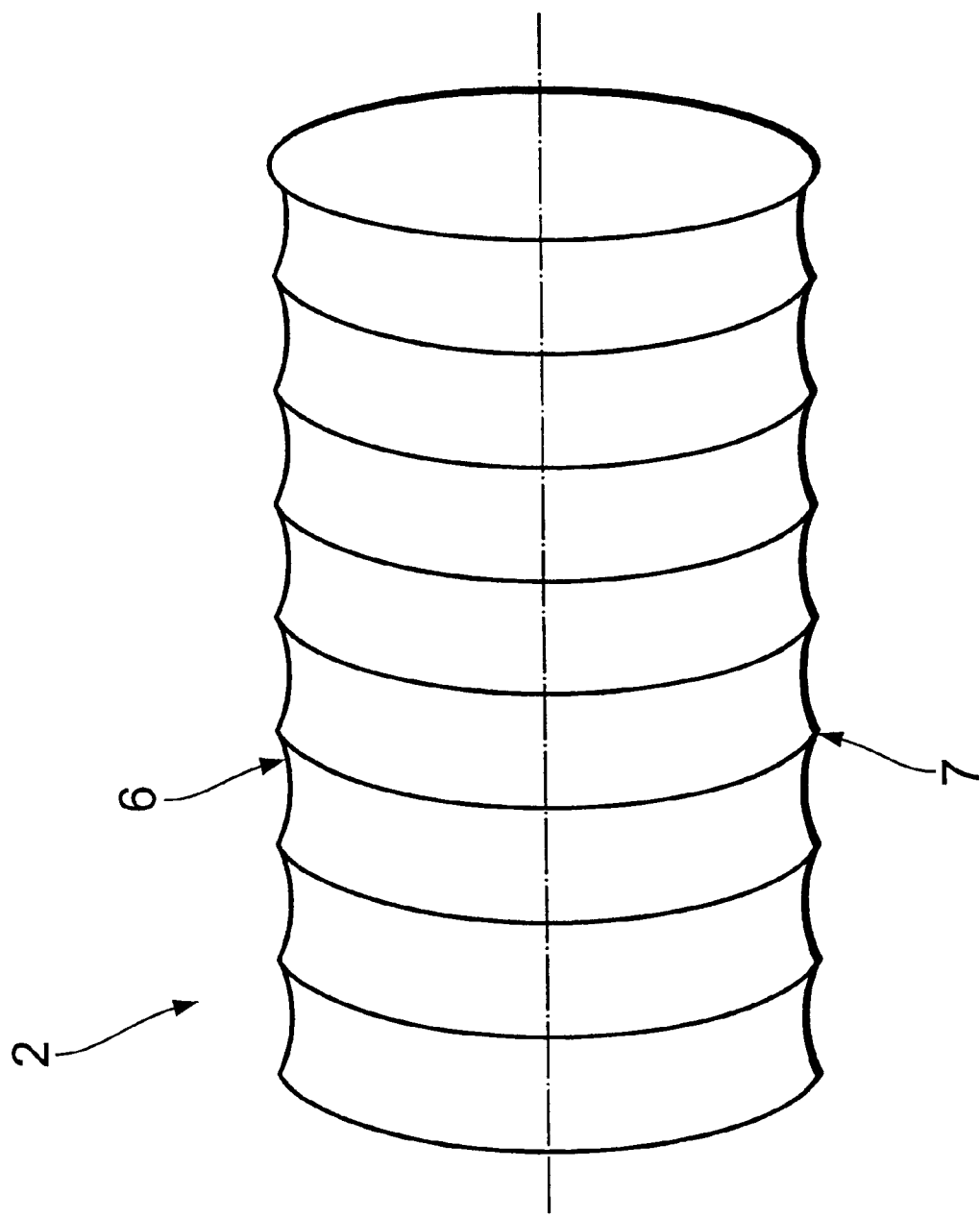
FIG. 1a shows an enlarged view of a part of FIG. 1.

Referring to FIG. 1, in a first embodiment 1 of a crimping device a stent-catheter combination 60 is put into a loop of a circulating endless belt 8. The belt 8 runs between two rollers 2 and 4 which correspond to the roller 2 illustrated in FIG. 1a. The rollers each have peripherally extending ribs 7 on their surfaces 6. They are mounted on rigid shafts in such a way that there is between the rollers only a narrow gap which prevents the stent-catheter combination 60 from passing between the rollers 2, 4. The drive roller 10 causes the endless belt 8 to rotate. By virtue of that rotation 11, the rollers 2 and 4 are caused to rotate in the direction of the arrows 14 and 16. At the same time the drive roller 10 is subjected to a force 12 which tensions the belt 8 and thus urges the stent-catheter combination 60 into the intermediate space 15 between the rollers 2 and 4. In that way the corrugation profile 6 of the rollers 2 and 4 is transferred onto the stent-catheter combination 60.

Figure 2:
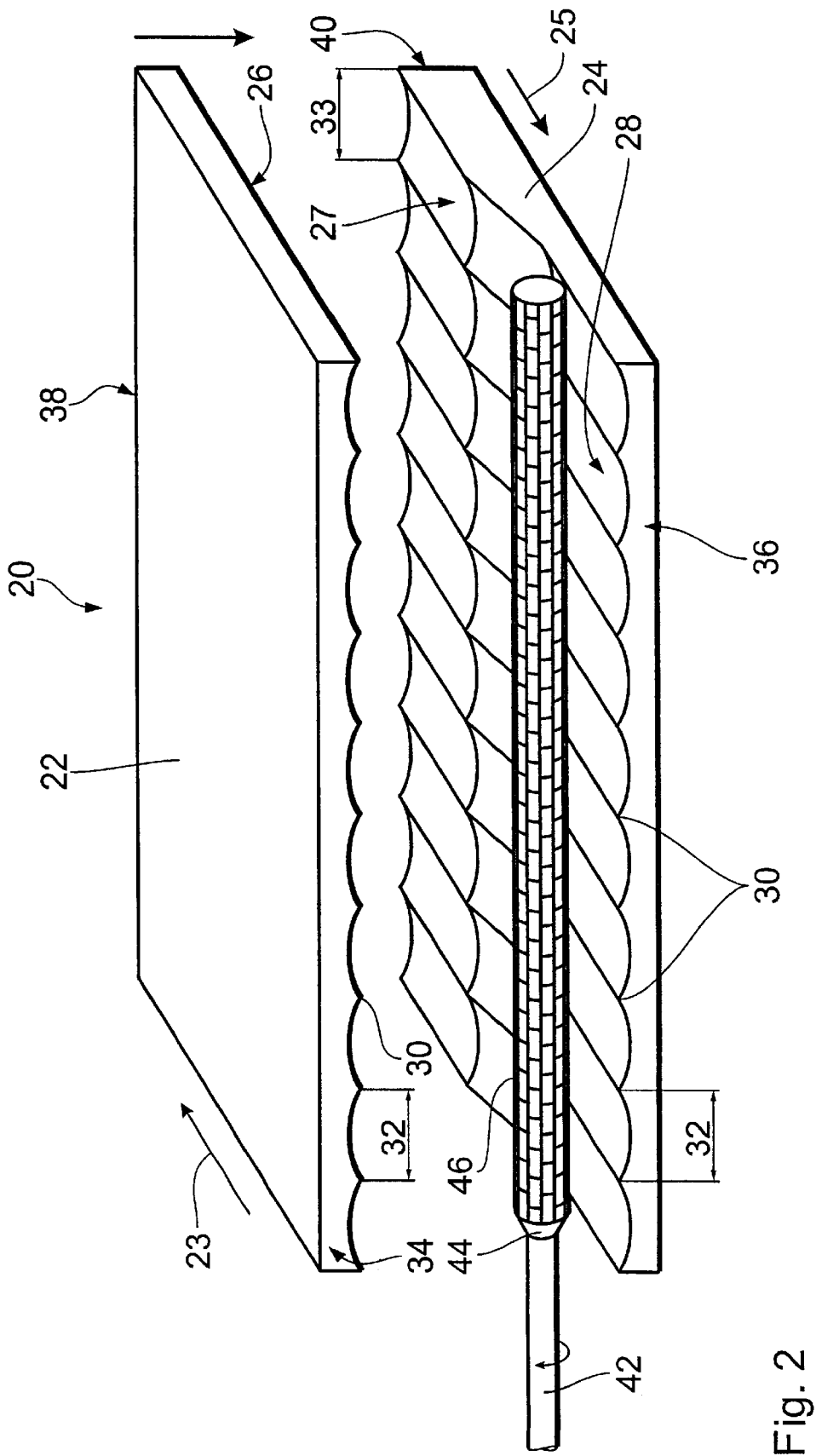
FIG. 2 shows a second embodiment of a crimping device according to the invention.

FIG. 2 shows a second embodiment 20 of a crimping device. As its pressing means, the crimping device 20 has an upper plate 22 and a lower plate 24 which is arranged substantially parallel to the upper plate 22. The mutually facing surfaces 26 and 28 respectively of the plates 22 and 24 have the corrugation shown in FIG. 2, in which respect the surface 26 and 28 respectively are of a substantially wave-shaped configuration, but with the wave crests 30 being of such a configuration as to converge a point. The spacing 32 of the wavecrests 30 at the sides 34 and 36 is equal to the spacing 33 of the wavecrests 30 at the rear sides 38 and 40 respectively of the plates 22 and 24 respectively. Crimping is effected by the corrugated plates 22 and 24 being displaced relative to each as indicated by the arrows 23 and 25. Due to the step 27 provided in the lower plate 24 the spacing of the plates 22 and 24 decreases during their oppositely directed movement so that it is not necessary for the plates 22, 24 also to be moved towards each other during such movement.

Alternatively, the spacing 32 of the wavecrests 30 can increase from the front sides 34 and 36 respectively of the plates 22 and 24 to the spacing 33 at the rear sides 38 and 40 respectively of the plates 22 and 24 as the stent 46 is increased in length upon compression of the balloon catheter 42, which is to be clamped between the plates 22 and 24, with the stent 46 carried on a balloon 44. In this alternative embodiment, this ensures that the crests 30, that is to say the locations at which crimping is greater, act on the stent 46 at the same location on the stent 46. The stent 46 is preferably a stent 46 which comprises segments (see also FIG. 4).

Figure 3:
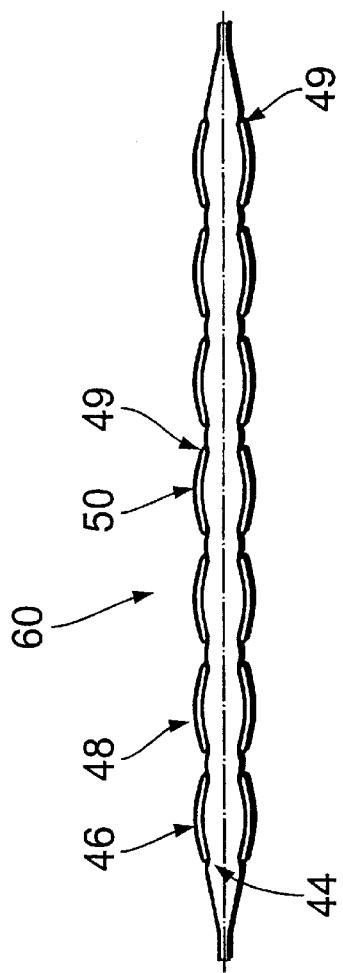
FIG. 3 shows a combination according to the invention of stent and balloon.

FIG. 3 shows a combination 60 of a stent 46 and a balloon 44, produced by means of the crimping device 20 illustrated in FIG. 2, with the stent having segments 48. FIG. 3 clearly shows that the edges 49 are crimped onto the balloon 44 more greatly than the central region 50 of the segments so as to impart a wave-shaped profile to the stent 46. If alternatively the stent 46 is a non-segmented stent, a suitable configuration for the surfaces of the rollers 2, 4 (FIG. 1) or plates 22, 24 (FIG. 2) means that it is possible to produce a scale-shaped profile on the peripheral surface thereof so that the sliding movement of such a stent in the vessel is improved.

Figure 4:
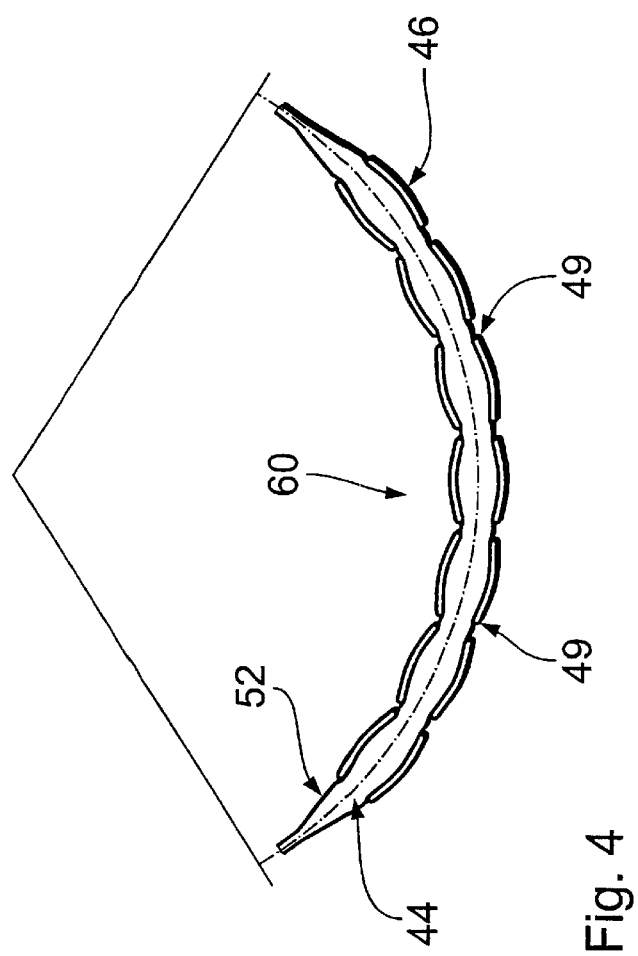
FIG. 4 shows the combination of FIG. 3 upon curvature thereof.

FIG. 4 clearly shows the action of the present invention. When the combination 60 comprising the balloon 44 and the stent 46 as shown in FIG. 3 is curved, the edges 49 of the segments 48 do not stand away from the surface 52 of the balloon 44, as in the state of the art; on the contrary, the edges 49 of the segments 48 remain against the surface 52 of the balloon 44 so that damage to the vessels when inserting such a combination 60 is avoided.

Figure 5:
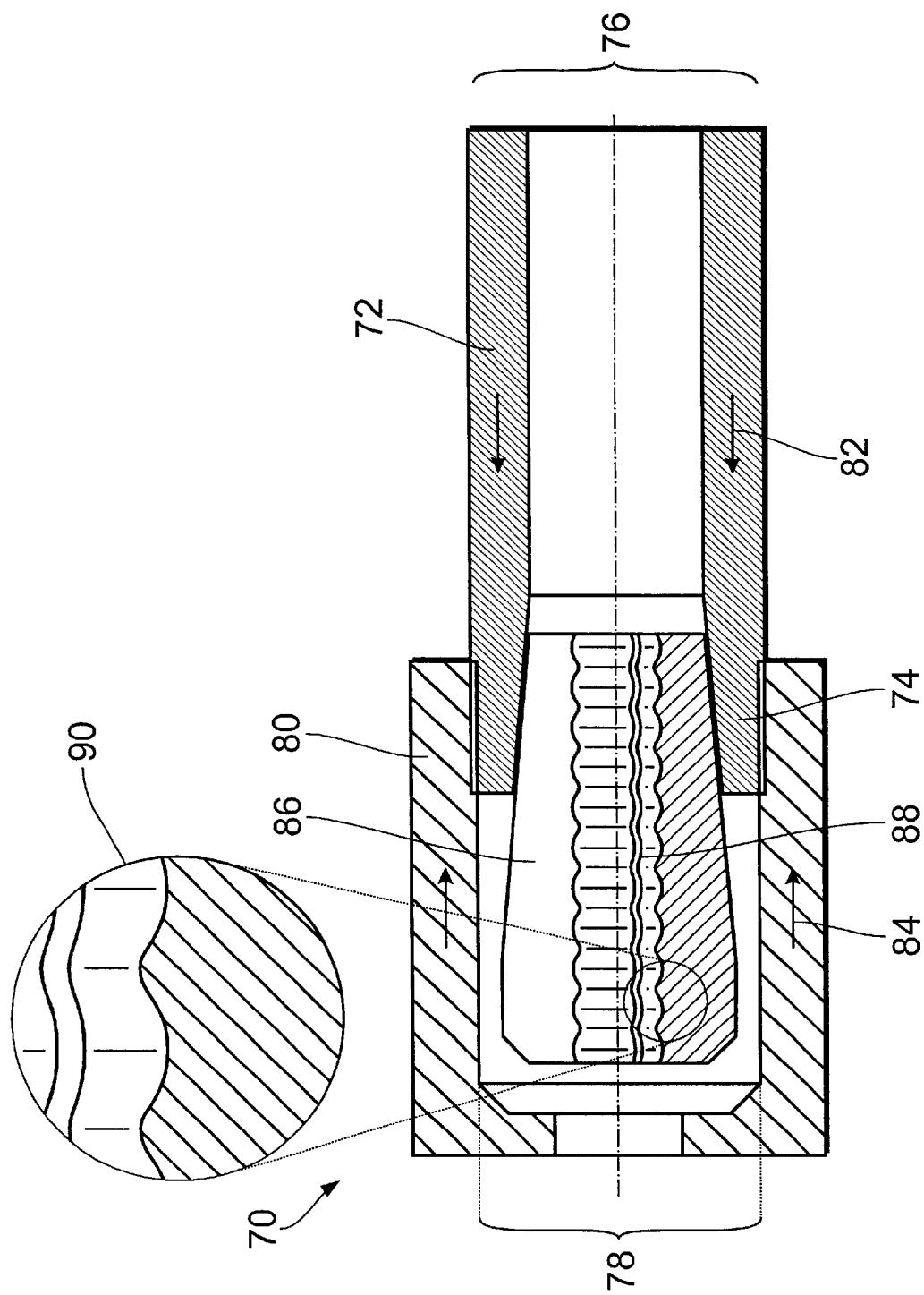
FIG. 5 shows a further embodiment of a crimping device.

FIG. 5 shows a further embodiment 70 of a crimping device according to the invention. The crimping device 70 is essentially formed by a collet. The collet comprises a hollow cylinder 72 which, at its end which is shown at the left in FIG. 5, is of a steadily taperingly decreasing wall thickness. The outside diameter 76 of the hollow cylinder 72 is adapted to the inside diameter 78 of a second hollow cylinder 80 so that the hollow cylinder 72 can be introduced into the second hollow cylinder 80 as indicated by the arrows 82. Likewise the second hollow cylinder 80 can be pushed onto the first hollow cylinder 72 as indicated by the arrows 84.

The beveled inside wall at the end 74 of the hollow cylinder 72 is adapted to the profile of jaws 86 which are disposed in the hollow cylinder 80. The jaws 86 are designed in the manner of a collet chuck comprising 3, 4 or more jaws, as are known from drilling machines or lathes. By virtue of the movement of the hollow cylinder 72 into the hollow cylinder 80, the jaws 86 are compressed and a stent-catheter combination within the cavity 88 between the jaws is in that way crimped by means of the jaws 86.

The portion 90 shows on an enlarged scale the corrugated internal surface of the jaws 86 so that the stent is crimped to a degree which alternates along its longitudinal axis.

It is particularly advantageous if the stent is crimped in two stages, that is to say, firstly to produce a large variation in diameter with a crimping device 1 as shown in FIG. 1 and then to produce a fine variation in diameter with a collet 70 as shown in FIG. 5.

Figure 6:
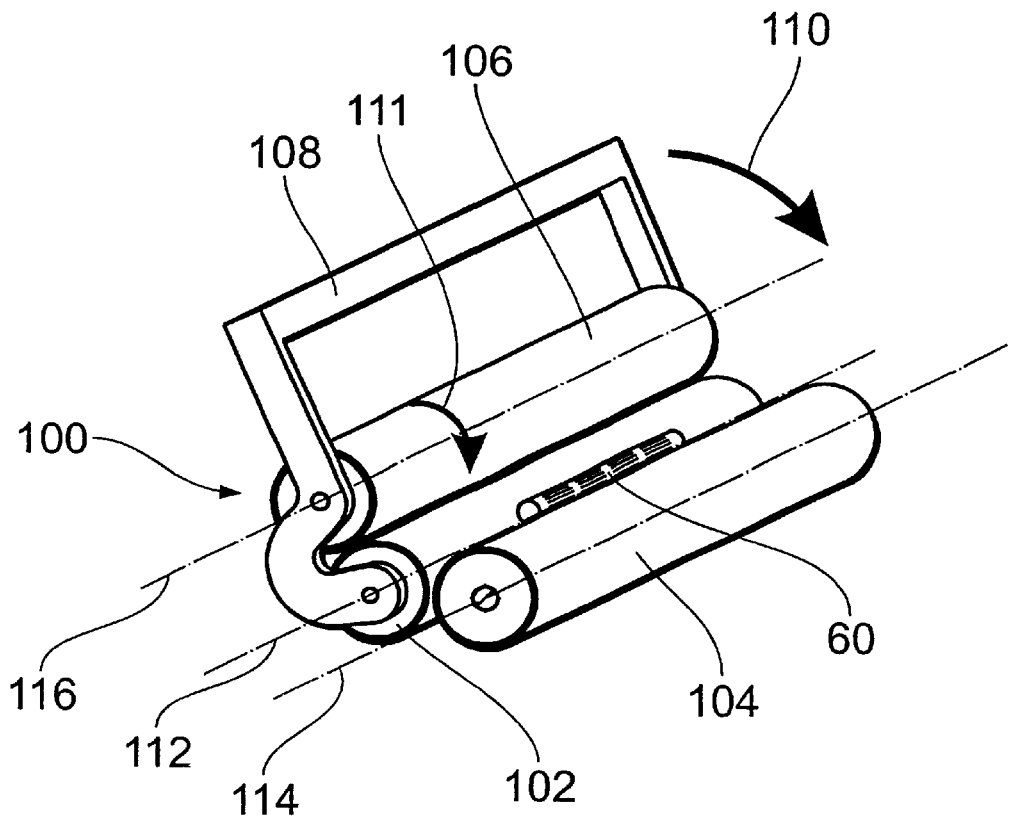
FIG. 6 shows a further embodiment of a crimping device.

FIG. 6 shows a further embodiment 100 of a crimping device. The crimping device 100 is shown as a perspective view in FIG. 6. The crimping device 100 has three rollers 102, 104 and 106. The rollers 102, 104 and 106 are arranged with their longitudinal axes 112, 114 and 116 respectively in mutually parallel relationship. In this case the rollers 102 and 104 are supported rigidly. The roller 106 is connected to the roller 102 by way of a pivot lever 108 and is pivotable by means of the pivot lever 108 about the axis 112 of the roller 102 in the direction indicated by the arrow 110. The spacing between the rollers 102 and 104 is so selected that the stent-catheter combination 60 cannot drop through the intermediate space between the rollers 102 and 104, even when the combination is in the crimped condition. In addition the roller 106 is connected to a drive (not shown) to cause it to rotate about its longitudinal axis 116 in the direction of the arrow 111.

Figure 7:
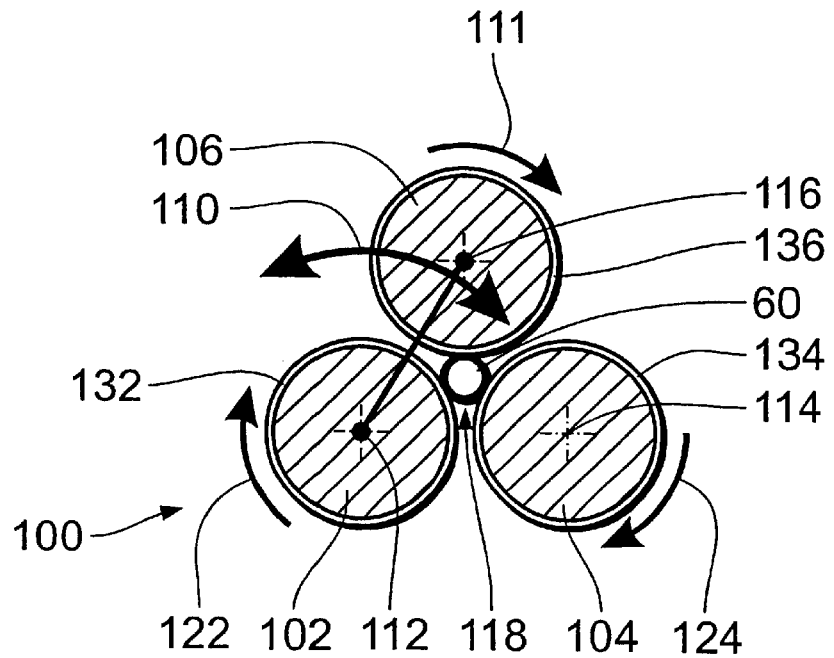
FIG. 7 is a view in cross-section of the embodiment of FIG. 6.

The mode of operation of the crimping device 100 will now be described with reference to FIG. 7. FIG. 7 is a view of the crimping device 100 of FIG. 6 in cross-section. Parts which correspond to those of FIG. 6 are denoted by the same references in FIG. 7. In order to crimp the stent-catheter combination 60 it is put into the entry nip or pinch 118 between the rollers 102 and 104. The roller 106 is then pivoted by means of the lever 108 shown in FIG. 6 about the longitudinal axis 112 of the roller 102 as indicated by the arrow 110 in order in that way to press the stent-catheter combination 60 into the nip 118 between the rollers 102 and 104. At the same time the roller 106 is caused to rotate about its longitudinal axis 116 as indicated by the arrow 111 by means of a drive (not shown). In that way, the stent-catheter combination 60 is caused to rotate, whereby in turn the rollers 102 and 104 are also caused to rotate about their longitudinal axes 112 and 114 respectively as indicated by the respective arrows 122 and 124. Due to the force applied by the roller 106 the stent-catheter combination 60 is compressed in the nip 118 between the surfaces 132, 134 and 136 of the rollers 102, 104 and 106 respectively. In order to crimp the stent-catheter combination 60 to varying degrees along its longitudinal axis, the surfaces 132, 134 and 136 of the respective rollers 102, 104 and 106 are of a corrugated configuration in the manner shown in FIG. 1*a*.

The embodiment 100 of the crimping device according to the invention as shown in FIGS. 6 and 7 affords the advantage that, by means thereof, in particular coronary stents which in comparison with peripheral stents involve a more filigree design can be crimped without any problem, without excessive forces being applied to the coronary stent.

What is claimed is:

1. A method of crimping a stent onto a balloon of a balloon catheter, comprising the steps of:

arranging the stent on the balloon so that an outside surface of the balloon and an inside surface of the stent contact each other, forming a combination of balloon and stent, and compressing the combination to crimp the stent onto the balloon by guiding the combination in a belt clamped between a pair of rollers and drawing the combination with the belt into an entry nip of the rollers where the combination is compressed the rollers being at an alternately increasing and decreasing spacing relative to each along the respective axes of rotation thereof, wherein the combination is compressed to differing degrees along a longitudinal axis thereof.

2. The method of claim 1, wherein the compressing step further comprises passing the combination between a pair of plates arranged in substantially mutually parallel relationship, a relative displacement of the pair of plates compressing the combination.

3. The method of claim 2, wherein the pair of plates are at an alternately increasing and decreasing spacing relative to each other, perpendicular to the direction of displacement of the plates.

4. The method of claim 1, wherein the compressing step further comprises driving at least one of the rollers about a longitudinal axis thereof to produce a rotary movement.

5. A stent, manufactured by the method of claim 1.

6. A device for crimping a stent onto a balloon of a balloon catheter, comprising:

a belt clamped between a pair of rollers having an entry nip, the belt being adapted for drawing into the entry nip a combination of the balloon and the stent, in which combination the stent is arranged on the balloon so that an outside surface of the balloon and an inside surface of the stent contact each other to form the combination, to compress the combination and to crimp the stent onto the balloon, wherein the pair of rollers are at an alternately increasing and decreasing spacing relative to each other along a longitudinal axis of the combination arranged therebetween.

7. The device of claim 6, wherein:

each said, roller is provided along a periphery thereof with a corrugated surface;

the rollers arranged with an axis of rotation of each in substantially mutually parallel relationship with the other, so that the combination is drawn into an entry nip of the rollers and is compressed thereby.

8. The device of claim 6, wherein:

the spacing between the rollers is smaller than a diameter of the combination in the crimped condition.

9. The device of claim 6, further comprising:

a drive for producing rotary motion about a longitudinal axis is connected to at least one of the rollers.

* * * * *